(12) United States Patent
Goldhahn et al.

(10) Patent No.: US 6,645,212 B2
(45) Date of Patent: Nov. 11, 2003

(54) DEVICE FOR FIXING IMPLANTS ON OR IN A BONE

(75) Inventors: Jörg Goldhahn, Davos (CH); Reto Frei, Davos (CH); Jörn Seebeck, Davos (CH)

(73) Assignee: Synthes (U.S.A.), Paoli, PA (US)

( * ) Notice: Subject to any disclaimer, the term of this patent is extended or adjusted under 35 U.S.C. 154(b) by 0 days.

(21) Appl. No.: 10/273,166

(22) Filed: Oct. 18, 2002

(65) Prior Publication Data
US 2003/0083663 A1 May 1, 2003

Related U.S. Application Data

(63) Continuation of application No. PCT/CH00/00229, filed on Apr. 20, 2000.

(51) Int. Cl.⁷ .............................................. A61B 17/58
(52) U.S. Cl. ........................................................ 606/73
(58) Field of Search ......................... 606/72, 73, 232, 606/66, 62, 65, 67; 411/411, 412, 453, 454

(56) References Cited

U.S. PATENT DOCUMENTS

| | | | | |
|---|---|---|---|---|
| 382,072 A | * | 5/1888 | Cavalli | 411/453 |
| 2,269,708 A | * | 1/1942 | Dickson | 411/453 |
| 2,649,009 A | * | 8/1953 | Selby | 411/453 |
| 4,637,768 A | * | 1/1987 | Rabe | 411/452 |
| 4,861,206 A | * | 8/1989 | Riedel | 411/36 |
| 5,053,035 A | | 10/1991 | McLaren | 606/67 |
| 5,180,382 A | | 1/1993 | Frigg et al. | 606/65 |
| 5,222,847 A | * | 6/1993 | Hiyama et al. | 408/222 |
| 5,383,905 A | * | 1/1995 | Golds et al. | 606/232 |
| 5,486,176 A | * | 1/1996 | Hildebrand et al. | 606/71 |
| 5,725,581 A | | 3/1998 | Brånemark | 623/16 |
| 5,728,116 A | | 3/1998 | Rosenman | 606/151 |
| 5,807,396 A | | 9/1998 | Raveh | 606/69 |
| 6,036,701 A | | 3/2000 | Rosenman | 606/151 |
| 6,187,007 B1 | | 2/2001 | Frigg et al. | 606/72 |

FOREIGN PATENT DOCUMENTS

| | | |
|---|---|---|
| EP | 0 663 184 A1 | 7/1995 |
| GB | 1 219 237 | 1/1971 |
| WO | WO 98/05263 | 2/1998 |

* cited by examiner

Primary Examiner—Michael J. Milano
Assistant Examiner—Daniel J Davis
(74) Attorney, Agent, or Firm—Pennie & Edmonds LLP

(57) ABSTRACT

The present invention concerns a fastening element for use in bone, and in particular to a device for fixating implants on or in bone. The device may have a longitudinal axis for anchoring in bone and may comprise a core and at least one wing extending from the core. The wing may have an enlarged peripheral portion adapted to contact bone. A cross-section of the device transverse to the longitudinal axis may have first and second portions, the first portion comprising the core and defining a first cross-sectional area, the second portion comprising the enlarged peripheral portion of the at least one wing and defining a second cross-sectional area, and the second cross-sectional area preferably is greater than the first cross-sectional area. The ratio of the second portion to the first portion preferably being at least about 3:1.

25 Claims, 5 Drawing Sheets

DEVICE FOR FIXING IMPLANTS ON OR IN A BONE

CROSS-REFERENCE TO RELATED APPLICATIONS

This application is a continuation of the U.S. national stage designation of copending International Patent Application PCT/CH00/00229, filed Apr. 20, 2000, the entire content of which is expressly incorporated herein by reference thereto.

FIELD OF THE INVENTION

The present invention concerns a fastening element for use in bone, and in particular to a device for fixating implants on or in bone.

BACKGROUND OF THE INVENTION

Implants have generally been anchored in the bone by means of screws, more recently also by means of monocortical screws anchored in an angularly stable manner. These screws have been designed, as far as their form is concerned, for use in healthy bone. In fact, the ratio between the cortical screws and the thickness of the corticalis has been optimized for enabling the best possible transmission of the occurring strains. These angularly stable screws no longer have the function of tension screws in the classical sense of the term but rather that of bolts. However, the screws currently in use for these purposes have dimensions which are optimized for use in healthy bone. As a consequence, the angularly stable screws, due to a reduced ratio between core diameter and outside diameter, are characterized by inferior strip forces and failure strains. A need therefore exists for an innovative means to anchor implants in bone.

SUMMARY OF THE INVENTION

The present invention is directed to a fastening element for use in bone, and in particular to a device for fixating implants on or in bone. The device may have a longitudinal axis and may comprise a core and at least one wing extending from the core. The wing may have a peripheral enlargement adapted to contact bone. A cross-section of the device transverse to the longitudinal axis may also have first and second portions, the first portion comprising the core, the second portion comprising the peripheral enlargement of the at least one wing. The second portion preferably is greater than the first portion. The ratio of the second portion to the first portion may preferably be at least about 3:1

In general, the device may have a plurality of wings and at least one of the peripheral enlargements may have a cross-section with a perimeter having at least one curved segment. The device may have peripheral enlargements which are substantially the same, and the peripheral enlargements may be arranged substantially in radial symmetry about the core. The peripheral enlargements may also be substantially point symmetric.

The core of the device may also comprise a free end having a coupling portion configured and dimensioned to join with an implant. The coupling portion may be adapted to contact a surface of the implant in positive engagement, or the coupling portion may be adapted to contact a surface of the implant in non-positive engagement. The coupling portion may also include a closing mechanism that is capable of securing the device to the implant. The closing mechanism may be capable of releasably securing the device to the implant. The implant may comprise a bone plate that may have a bore which is configured and dimensioned to correspond with the cross-section of the device to allow an angularly stable anchoring of the device in the bone plate.

The core may also be provided with a bore, which may have a cross-section that is substantially circular. For instance, the bore may have a diameter of about 2 mm. The device may also be spirally twisted. For example, the spirally twisted portion of the device may comprise a length of about 8 mm to about 12 mm, and the spirally twisted portion may be twisted relative to the longitudinal axis by about 100 to about 140 degrees.

The device may have a cross-section that has a moment of inertia about a first coordinate axis and a moment of inertia about a second coordinate axis, the first and second coordinate axes being orthogonal to the longitudinal axis of the device, and the ratio of the maximum moment of inertia to the minimum moment of inertia about the first and second axes being less than or equal to about 5:1.

The device may be a bone screw comprising a core, having a bore with a diameter and an inner surface disposed concentrically about the longitudinal axis of the screw. At least one wing may extend from the core, the at least one wing having a peripheral enlargement adapted to contact bone. The core and the at least one wing may be contained in an imaginary cylinder having a central axis coincident with the longitudinal axis. The imaginary cylinder may abut the at least one wing and may have a diameter such that a ratio of the diameter of the bore divided by the diameter of the imaginary cylinder is less than or equal to about 0.5. In one embodiment, the ratio between the diameter of the bore and the diameter of the imaginary cylinder preferably is less than or equal to about 0.30.

In general, a line segment from a point on the inner surface of the bore to a point on the imaginary cylinder may define a length equal to one-half the diameter of the imaginary cylinder minus one-half the diameter of the bore. In addition, a cross-section of the device transverse to the longitudinal axis may have an outer surface portion and an inner surface portion. The outer surface portion may be located within a first imaginary annulus having an outer diameter equal to the diameter of the imaginary cylinder, and an inner diameter equal to the length of the line segment from a point on the inner surface of the bore to a point on the imaginary cylinder. The inner surface portion may be located within a second imaginary annulus having an outer diameter equal to the inner diameter of the first imaginary annulus and an inner diameter equal to the diameter of the bore. In one example, the ratio of the outer surface portion to the inner surface portion may be at least about 3:1. In another example, the ratio of the outer surface portion to the inner surface portion may be at least about 3.5:1. In yet another example, the ratio of the outer surface portion to the inner surface portion may be at least about 4.0:1.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE PREFERRED EMBODIMENTS

Figure 1:
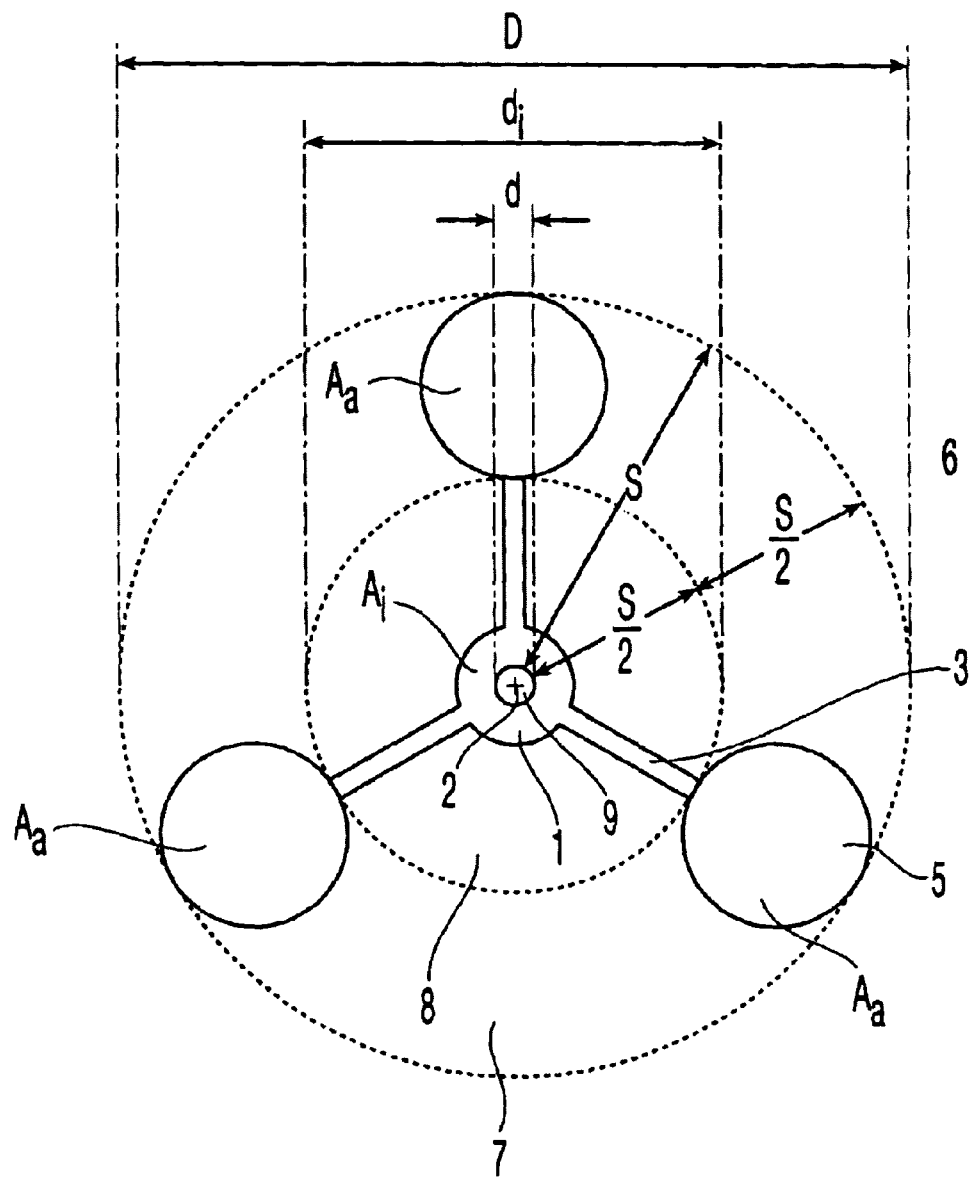
FIG. 1 is a cross-section of an exemplary embodiment of a device for fixation of implants on or in bone according to the present invention.

For convenience, the same or equivalent elements in the various embodiments of the invention illustrated in the drawings have been identified with the same reference numerals. Further, in the description that follows, any reference to either orientation or direction is intended primarily for the convenience of description and is not intended in any way to limit the scope of the present invention thereto.

Referring to FIG. 1, in an illustrative embodiment, the diagrammatic profile of the device comprises a hollow core 1 with a longitudinal axis 2 (extending vertically with respect to the plane of the drawing) and with three wings 3 extending radially therefrom and including peripheral enlargements 5. The core 1, wings 3, and enlargements 5 may be contained within an upright regular cylinder (extending vertically to the plane of the drawing) with an outside diameter D=2S+d and an identical longitudinal axis 2. The diameter d of the bore 9 formed in the core 1 is preferably 2 mm, the value S being between 3 mm and 50 mm, preferably between 5 mm and 30 mm.

Considered in a plane 6 extending orthogonally to the longitudinal axis 2, which corresponds to the plane of the drawing, the ratio $A_a/A_i$ existing between the outer surface portion $A_a$—located within the annulus 7 representing the difference between the areas of the two circles with the respective diameters D=2S+d and $d_i$=S+d extending concentrically to the longitudinal axis 2—and the inner surface portion $A_i$—located within the annulus 8 extending concentrically to the longitudinal axis 2 and representing the difference between the areas of the two circles with the respective diameters $d_i$ and d—of the cross-sectional surface $A=A_a+A_i$ of the implant located within the portion of the profile serving for the transmission of forces relative to the longitudinal axis 2 of the device, is at least 3:1. Typically, the ratio $A_a/A_i$ may be between about 3.5:1 and about 3.0:1.

Figure 2:
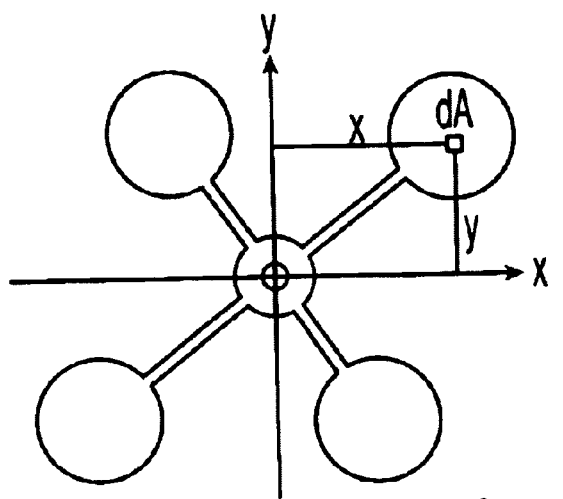
FIG. 2 is a cross-section of another embodiment of the device of FIG. 1, having a four-wing profile in an x/y coordinate system and including the formula for the calculation of different geometrical moments of inertia.

FIG. 2, shows a four-wing profile in an x/y coordinate system by means of which the calculation of the geometrical moments of inertia $I_x$, $I_y$ and $I_z$ is illustrated. In general, the ratio between the maximum and the minimum geometrical moments of inertia $I_{max}/I_{min}$ should not exceed a value of 5:1, and preferably should not exceed a value of about 4:1.

Figure 3:
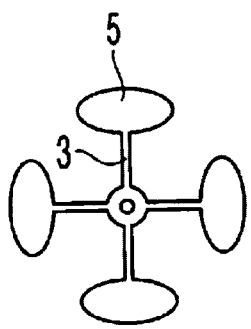
FIG. 3 is a cross-section of another embodiment of the device of FIG. 1, having a four-wing profile in an x/y coordinate system.
Figure 4:
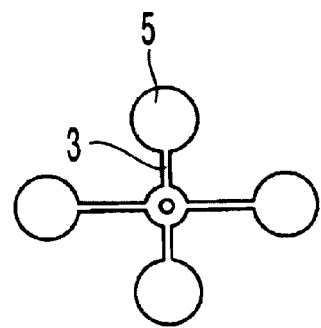
FIG. 4 is a cross-section of yet another embodiment of the device of FIG. 1, having a four-wing profile in an x/y coordinate system.
Figure 5:
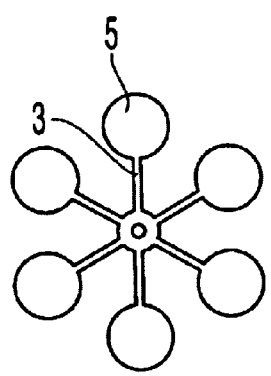
FIG. 5 is a cross-section of another embodiment of the device of FIG. 1 having a six-wing profile in an x/y coordinate system.

FIGS. 3–5, show non-limiting examples of other embodiments of the device 10. Specifically, FIG. 3 and FIG. 4 show different embodiments of a four-wing profile having enlargements of different shapes. In FIG. 3, the enlargements 5 are not circularly cylindrical but are shaped in the form of cylindroids. By contrast, FIG. 4 shows a profile which is similar to that of FIG. 3 but which is not point-symmetric. FIG. 5 shows an embodiment having a six-wing profile. Depending on the type of application, further profiles may be used, as long as they substantially fulfil the geometrical conditions stated above.

Figure 6:
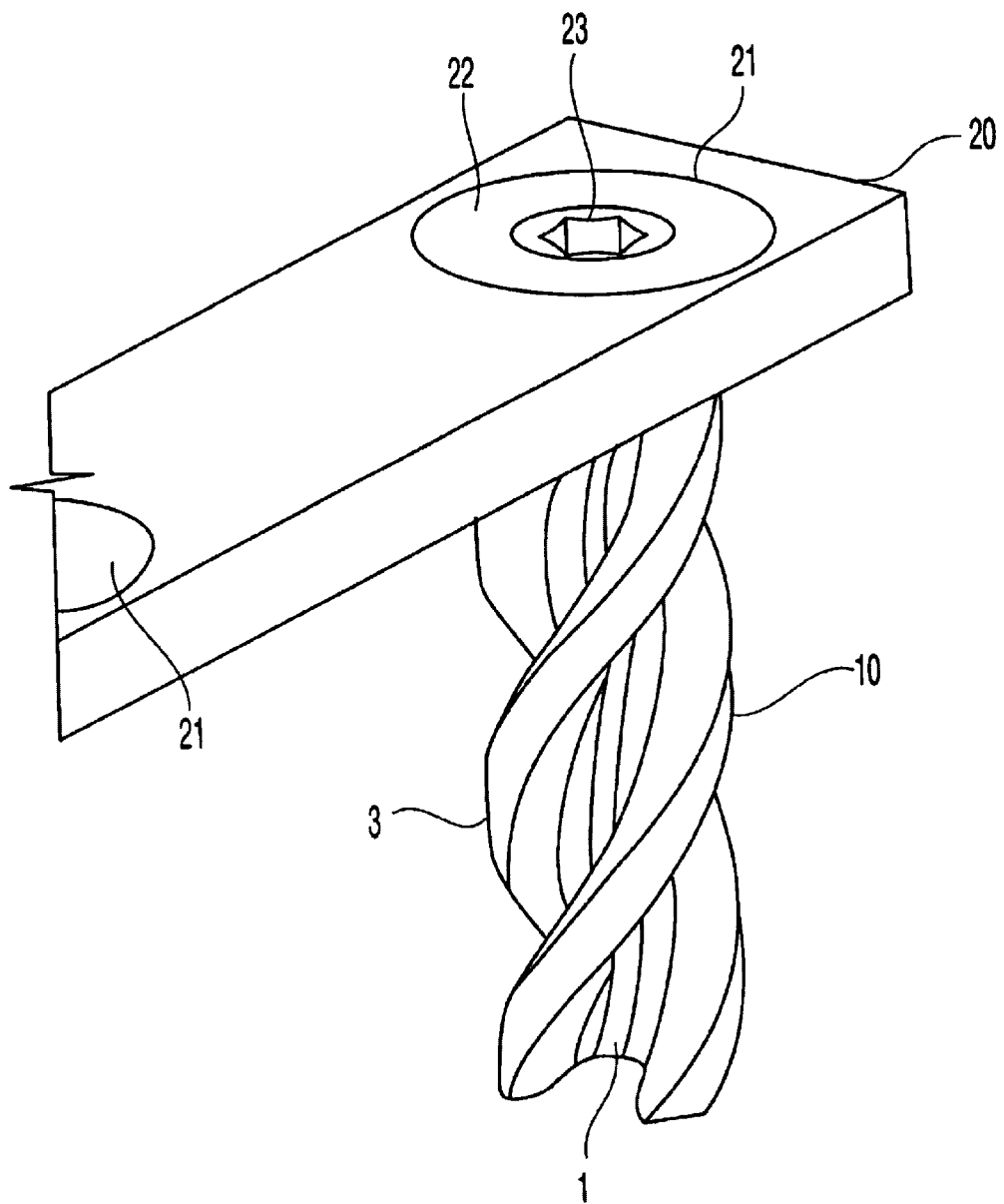
FIG. 6 is a perspective view of another embodiment of the device of FIG. 1 inserted into a bone plate.

FIG. 6 shows an illustrative embodiment of a device 10 according to the present invention. The device 10 may comprise a twisted profile having a core 1 and wings 3, shaped in the form of a bone screw. In addition, the device may be inserted into a bone plate 20 having a plurality of holes 21 for receiving one or more bone fastening elements. The shape of the holes 21 may be circularly cylindrical or have some other configuration. On one end, the device 10 may also include a head 22 which is adapted to be received within a hole 21 of the plate 20. The head 22 may be provided with a recess 23 for receiving a corresponding screw driver head to enable the device 10 to be readily screwed into bone. For example, the recess 23 may have a hexagonal shape that is adapted for use with a screw driver having a corresponding hexagonal shaped head (or driving member).

Figure 7:
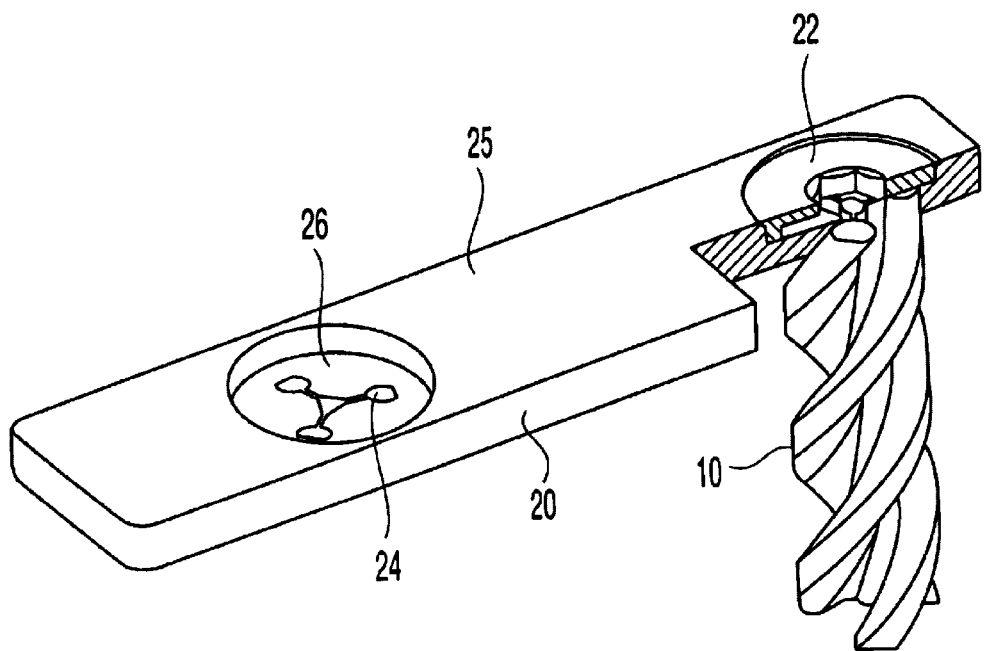
FIG. 7 is a partial sectional view of the device and bone plate of FIG. 6.

FIG. 7 shows the device 10 of FIG. 6 inserted into a bone plate 20 having holes comprising specially shaped clearances 24 which correspond to the cross-sectional profile of the device 10. In this embodiment of the bone plate 20, the clearances 24 are shaped in a tri-radiate form and are arranged in a recess formed in the surface 25 of the bone plate 20, permitting the head 22 of the device 10 to be completely sunk into the circularly cylindrical recess 26 of the bone plate 20 so as to be level with the surface 25. A positive engagement between the device 10 and the bone plate 20 may be achieved in this manner.

Thus, in an exemplary and non-limiting embodiment of the present invention, the device 10 may comprise a longitudinal, solid or hollow core 1 with a longitudinal axis 2 and a number of wings 3 extending radially therefrom. The device may be contained within an upright, regular cylinder with an outside diameter D=2S+d and an identical longitudinal axis 2 forming its envelope. Also, the cylinder has a predetermined radius (½ D) extending from a central axis coincident with the longitudinal axis. The dimension d may correspond to the diameter of an optional bore 9 formed in the core 1, and the dimension S may correspond to a value between 3 mm and 50 mm.

When considered in a plane 6 extending orthogonally to the longitudinal axis 2, an outer surface portion $A_a$ is defined as the surface area located within the annulus 7 and represents the difference between the areas of the two circles with the respective diameters D=2S+d and di=S+d, extending concentrically to the longitudinal axis 2. An inner surface portion $A_i$ is defined as the surface area located within the annulus 8 extending concentrically to the longitudinal axis 2 and represents the difference between the areas of the two circles with the respective diameters $d_i$ and d. The total cross-sectional surface $A=A_a+A_i$ of the implant located within the portion of the profile serves for the transmission of forces relative to the longitudinal axis 2 of the device, and the ratio $A_a/A_i$ may preferably be at least 3:1. In another embodiment of the device, the ratio $A_a/A_i$ may be at least 3.5:1, and in a preferred embodiment of the device, the ratio $A_a/A_i$ may be at least 4:1.

An illustrative embodiment of the device 10 may also be described in that the ratio between the maximal and the minimal geometrical moments of inertia $I_{max}/I_{min}$ should not exceed a value of 5:1. In a preferred embodiment, the device 10 may be described in that the ratio $I_{max}/I_{min}$ should not exceed a value of 4:1.

The above exemplary embodiments of the device 10 may also have on one of their free ends a coupling 4. The coupling, preferably, may be in the form of an enlarged profile portion which allows a positive or non-positive connection with another implant. The coupling 4 may comprise means which permit the device to be releasably locked within another implant in such a way as to be secured against displacement.

In general, exemplary embodiments of the device 10 may have at least two wings 3, and some preferred embodiments of the device 10 may have at least three wings 3. The free ends of the wings 3 may be equipped with enlarged peripheral portions 5. In addition, the cross-sectional profile of the device may be spirally twisted about the longitudinal axis. For example, the device 10 preferably may have a length of 8 mm to 12 mm, and the cross-sectional profile may be spirally twisted approximately 100 to 140 degrees, relative to the longitudinal axis 2. Also, the longitudinal core 1 of the device 10 may be provided with a bore 9 formed therein. The geometry of the longitudinal core 1 may be configured and dimensioned to relate to the overall dimensions of the device. For instance, the ratio d/D between the core diameter d and the outside diameter D=2S+d might not exceed a specified value. For example, the ratio d/D might not exceed 0.5. In another example, the ratio d/D might not exceed 0.33, and in one preferred embodiment of the device 10 the ratio d/D might not exceed 0.30.

The device 10 according to the present invention may also be used with a bone plate 20. For example, the bone plate may have at least two bores 11 formed therein which are adequately shaped so as to be capable of receiving the couplings 4 of the devices 10 in such a way that they are in positive or non-positive engagement.

While various descriptions of the present invention are described above, it should be understood that the various features can be used singly or in any combination thereof. Therefore, this invention is not to be limited to only the specifically preferred embodiments depicted herein. For instance, the foregoing embodiments are described on the basis of a bone plate having a generally rectangular cross-section, but a bone plate of any suitable configuration may also be used. Similarly, other specially shaped clearances in the bone plate may be may be used.

It should be understood that variations and modifications within the spirit and scope of the invention may occur to those skilled in the art to which the invention pertains. Thus, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A device for anchoring in bone having a longitudinal axis comprising:
    a core; and
    at least one wing extending from the core, the at least one wing having an enlarged peripheral portion adapted to contact bone,
    wherein a cross-section of the device transverse to the longitudinal axis has first and second portions, the first portion comprising the core and defining a first cross-sectional area, the second portion comprising the enlarged peripheral portion of the at least one wing and defining a second cross-sectional area, and the second cross-sectional area is greater than the first cross-sectional area.

2. The device of claim 1, wherein the device has a plurality of wings.

3. The device of claim 2, wherein at least one of the peripheral portions has a cross-section with a perimeter having at least one curved segment.

4. The device of claim 2, wherein the peripheral portions have substantially the same geometry.

5. The device of claim 2, wherein the peripheral portions are arranged substantially in radial symmetry about the core.

6. The device of claim 2, wherein the peripheral enlargements are substantially point symmetric.

7. The device of claim 1, wherein the core comprises a free end having a coupling portion configured and dimensioned to join with an implant.

8. The device of claim 7, wherein at least a part of the coupling portion is adapted to contact a surface of the implant in positive engagement.

9. The device of claim 7, wherein at least a part of the coupling portion is adapted to contact a surface of the implant in non-positive engagement.

10. The device of claim 7, wherein the coupling portion includes a closing mechanism that is capable of securing the device to the implant.

11. The device of claim 10, wherein the closing mechanism is capable of releasably securing the device to the implant.

12. The device of claim 7, wherein the implant comprises a bone plate.

13. The device of claim 12, wherein the bone plate has at least one bore that is configured and dimensioned to correspond with the cross-section of the device to allow an angularly stable anchoring of the device in the bone plate.

14. The device of claim 1, wherein at least a part of the core is provided with a bore.

15. The device of claim 14, wherein a cross-section of the bore is substantially circular.

16. The device of claim 14, wherein the bore has a diameter of about 2 mm.

17. The device of claim 1, wherein at least a portion of the device is spirally twisted.

18. The device of claim 17, wherein the spirally twisted portion comprises a length of about 8 mm to about 12 mm, and the spirally twisted portion is twisted relative to the longitudinal axis by about 100 to about 140 degrees.

19. The device of claim 1, wherein a ratio of the second cross-sectional area to the first cross-sectional area is at least about 3:1.

20. The device of claim 1, wherein the cross-section has a moment of inertia about a first coordinate axis and a moment of inertia about a second coordinate axis, the first and second coordinate axes being orthogonal to the longitudinal axis of the device, and the ratio of the maximum moment of inertia to the minimum moment of inertia about the first and second axes is less than or equal to about 5:1.

21. A bone screw having a longitudinal axis comprising:
    a core, at least part of the core having a bore with a radius and an inner surface disposed concentrically about the longitudinal axis of the device; and
    at least one wing extending from the core, the at least one wing having an enlarged peripheral portion adapted to contact bone,
    wherein the core and the at least one wing are within a predetermined radial distance from a central axis coincident with the longitudinal axis, the radial distance defining a right cylinder about the longitudinal axis wherein a ratio of the radius of the bore divided by the radial distance is less than or equal to about 0.5.

22. The bone screw of claim 21, wherein the ratio between the radius of the bore and the radial distance is less than or equal to about 0.30.

23. The bone screw of claim 21, wherein a line segment from a point on the inner surface of the bore to a point on the at least one wing tangential to the cylinder defines a first length equal to the radial distance of the cylinder minus the radius of the bore, and wherein a cross-section of the device transverse to the longitudinal axis has an outer surface portion and an inner surface portion, the outer surface portion being located within a first annulus having an outer diameter equal to twice the radial distance of the cylinder, and an inner diameter equal to the first length, the inner surface portion being located within a second imaginary annulus having an outer diameter equal to the inner diameter of the first imaginary annulus and an inner diameter equal to twice the radius of the bore, and a ratio of the outer surface portion to the inner surface portion is at least about 3:1.

24. The bone screw of claim 23, wherein the ratio of the outer surface portion to the inner surface portion is at least about 3.5:1.

25. The bone screw of claim 23, wherein the ratio of the outer surface portion to the inner surface portion is at least about 4.0:1.

* * * * *